(12) United States Patent
Longtain et al.

(10) Patent No.: US 9,700,355 B2
(45) Date of Patent: Jul. 11, 2017

(54) PEDICLE SCREW ASSEMBLY

(75) Inventors: Aaron M. Longtain, Saginaw, MI (US); Jeremy L. Longtain, Freeland, MI (US)

(73) Assignee: Aaron M. Longtain, Saginaw, MI (US)

( * ) Notice: Subject to any disclaimer, the term of this patent is extended or adjusted under 35 U.S.C. 154(b) by 901 days.

(21) Appl. No.: 13/303,193

(22) Filed: Nov. 23, 2011

(65) Prior Publication Data

US 2013/0131734 A1    May 23, 2013

(51) Int. Cl.
*A61B 17/70*    (2006.01)
(52) U.S. Cl.
CPC .......... *A61B 17/7037* (2013.01); *A61B 17/70* (2013.01); *A61B 17/7001* (2013.01); *A61B 17/7034* (2013.01)
(58) Field of Classification Search
CPC ............ A61B 17/7001; A61B 17/7032; A61B 17/7035; A61B 17/7037
USPC ................................................. 606/264–270
See application file for complete search history.

(56) References Cited

U.S. PATENT DOCUMENTS

| | | | |
|---|---|---|---|
| 5,207,678 | A | 5/1993 | Harms et al. |
| 8,197,518 | B2 | 6/2012 | Hammill, Sr. et al. |
| 2003/0153911 | A1* | 8/2003 | Shluzas ........................... 606/61 |
| 2005/0283157 | A1* | 12/2005 | Coates et al. ................... 606/73 |
| 2007/0270813 | A1* | 11/2007 | Garamszegi ..................... 606/61 |
| 2010/0016969 | A1* | 1/2010 | Richter et al. ............. 623/17.11 |
| 2011/0152949 | A1* | 6/2011 | Biedermann ...... A61B 17/7037 606/305 |
| 2012/0010658 | A1* | 1/2012 | Kirschman ................... 606/246 |
| 2012/0310284 | A1 | 12/2012 | Gerchow |
| 2013/0150852 | A1* | 6/2013 | Shluzas .............. A61B 17/7032 606/65 |

* cited by examiner

*Primary Examiner* — Nicholas Plionis
(74) *Attorney, Agent, or Firm* — Warner Norcross and Judd LLP

(57) ABSTRACT

A pedicle screw assembly having an axial load element engaging the structure joining the screw and the rod retainer. The axial load element generally holds the rod retainer in place with respect to the screw, while allowing manual movement when desired. In one embodiment, the pedicle screw assembly includes a ball-and-socket joint joining the screw head to the rod retainer. The assembly may include a saddle configured to secure a ball at the head of the screw within a socket in the rod retainer. The saddle may provide resilient compression in the axial direction. For example, the saddle may include a pair of axially-offset slots that extend partially across the saddle from opposite sides to define a bridge section. The resiliency of the saddle may be controlled by varying the characteristics of the slots and consequently the bridge section.

10 Claims, 9 Drawing Sheets

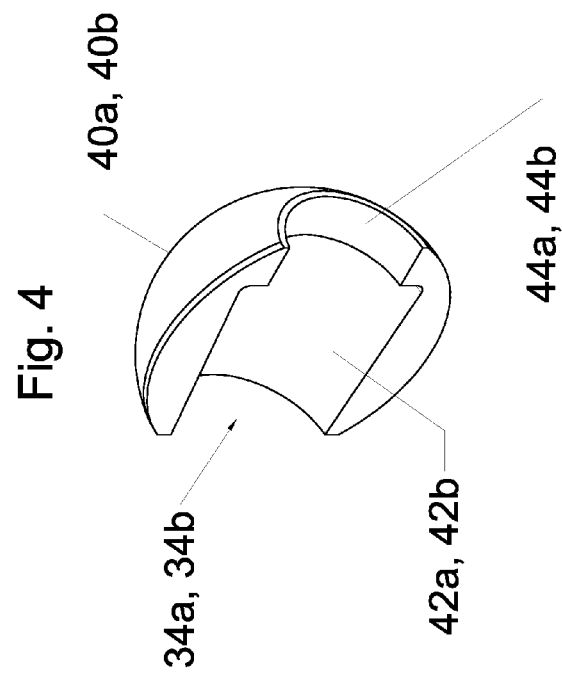
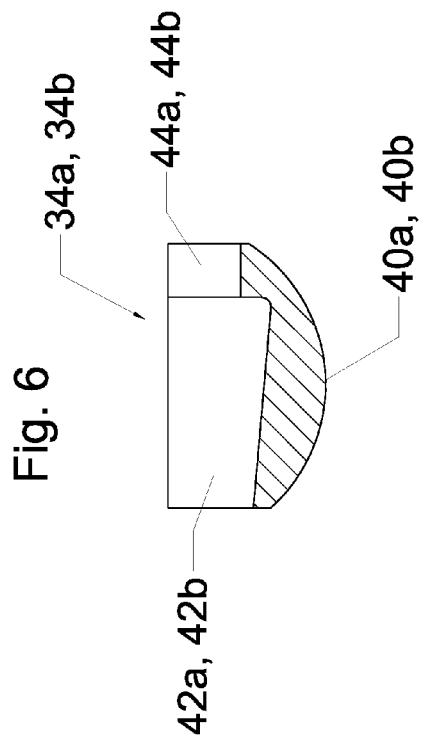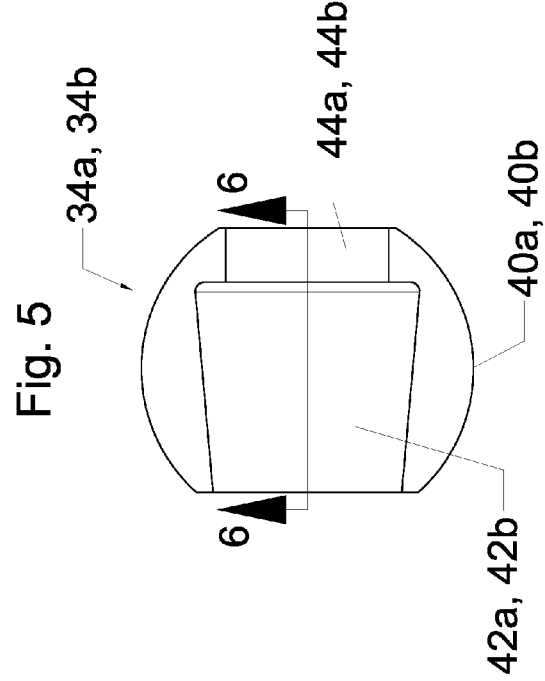

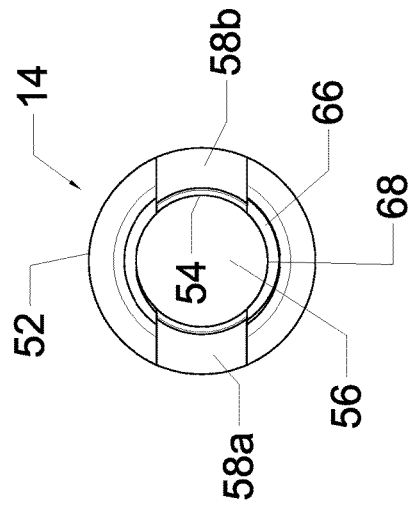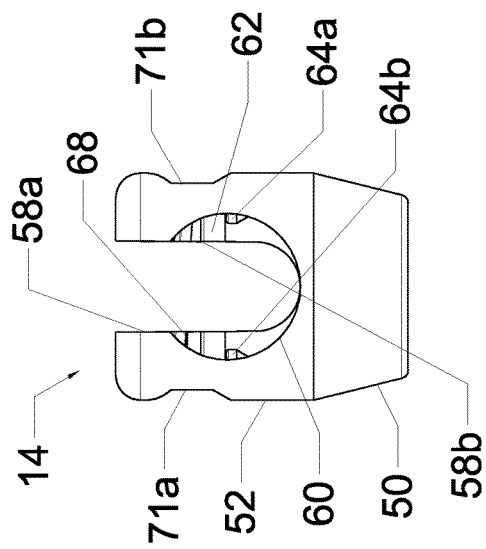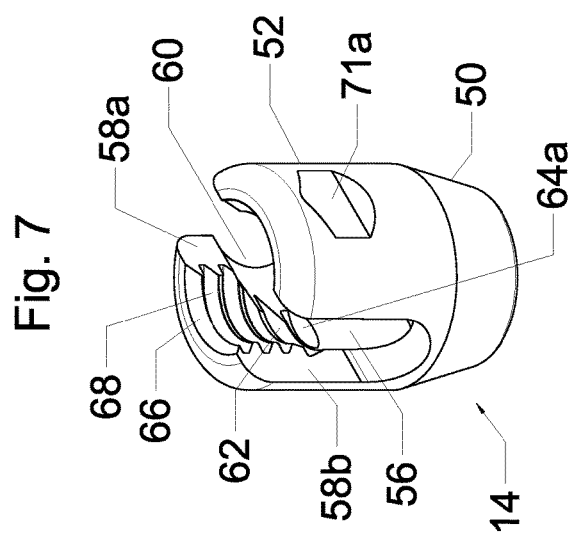

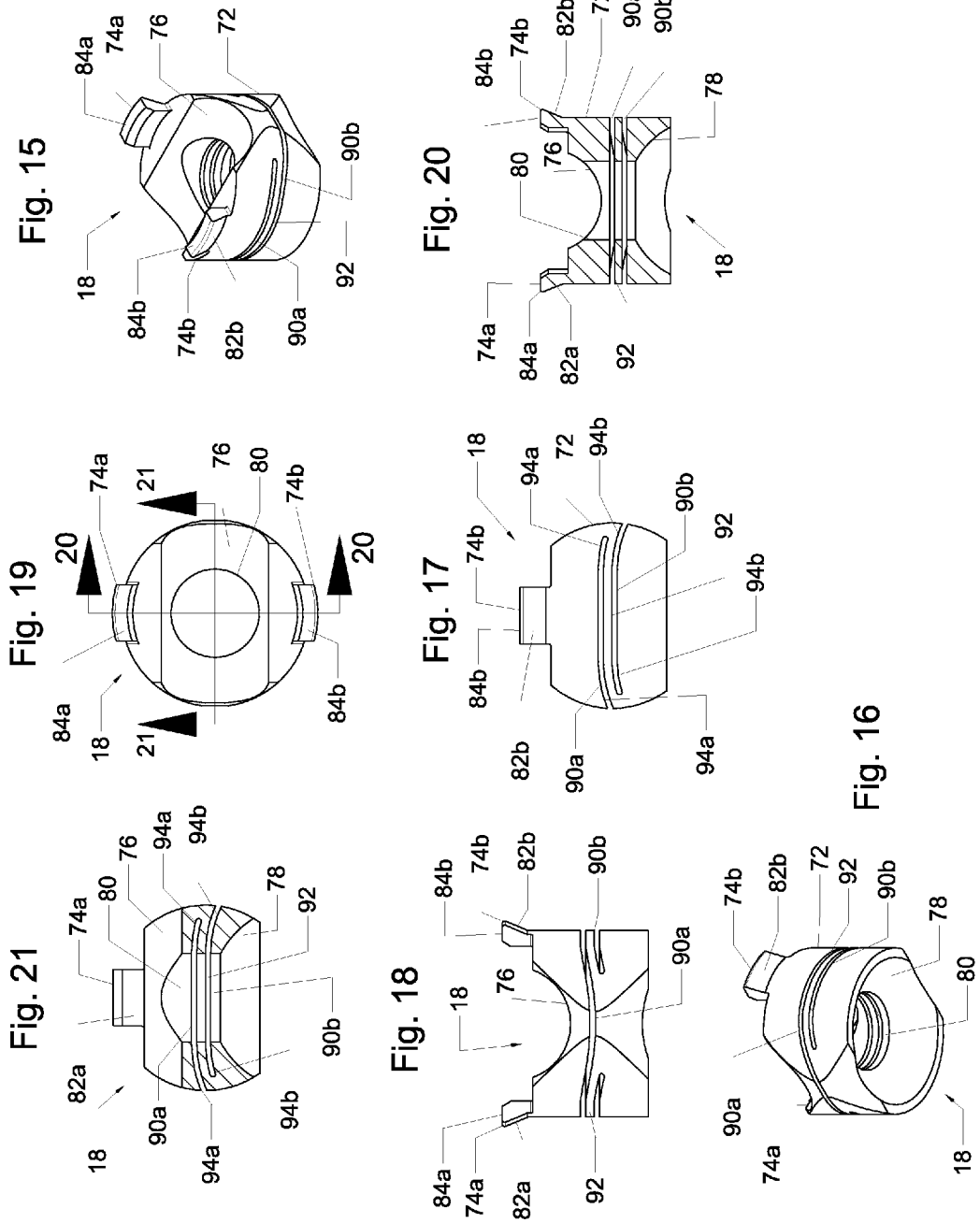

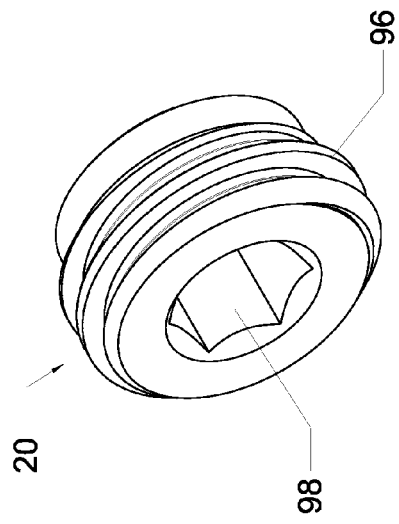
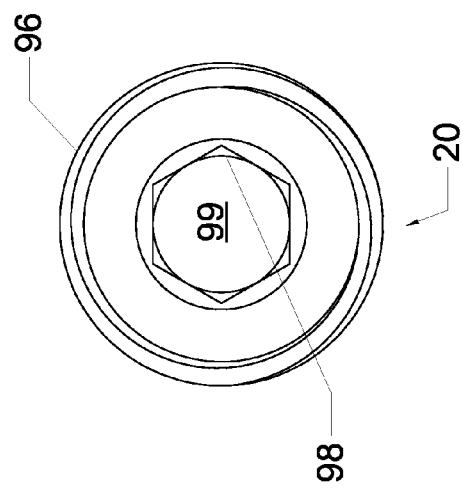
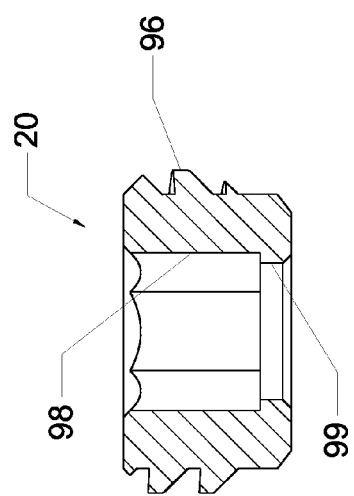

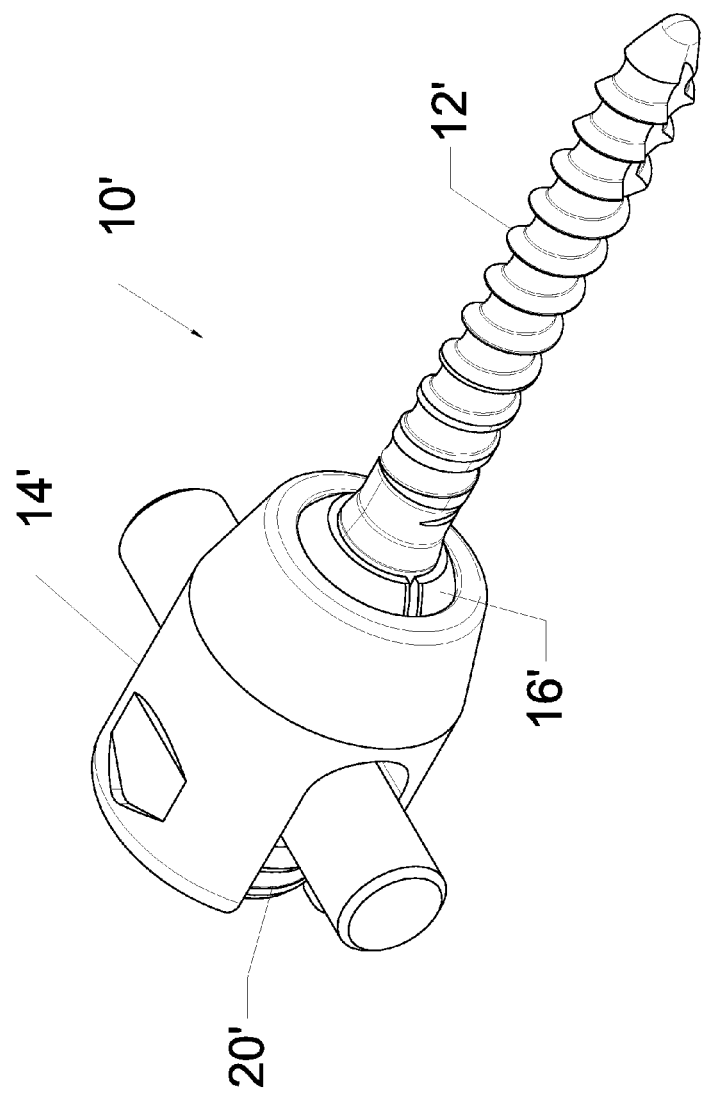

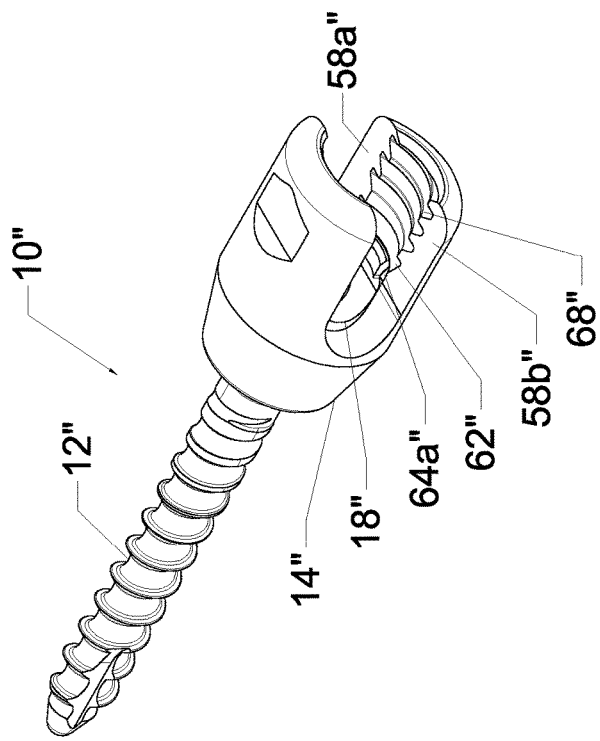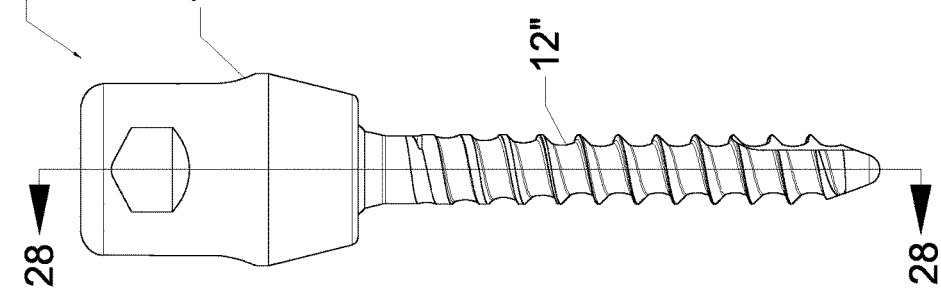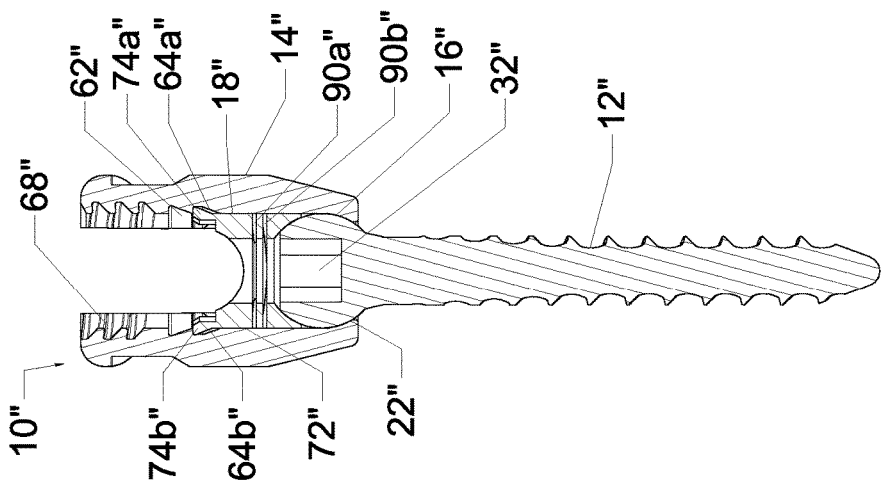

PEDICLE SCREW ASSEMBLY

BACKGROUND OF THE INVENTION

The present invention relates to medical screws, and more particularly to pedicle screw assemblies.

Pedicle screws are commonly used to assist in various forms of spinal fusion surgery. Spinal fusion surgery can be performed to correct a variety of spinal conditions caused by damage to or degeneration of a segment of the spine. Spinal fusion procedures typically involve fusing together segments of the spine to prevent conditions resulting from their relative movement. In a typical spinal fusion procedure, a portion of the spine is removed and bone grafts are implanted to form a bridge that joins the spine segments on opposite sides of the removed portion. Pedicle screws are used during this process to hold the spine segments to be fused so that the bone grafts can heal and form a solid bridge. More specifically, pedicle screws are installed in spinal segments to provide anchor points that allow the spinal segments to be fixedly connected with rods. For example, in a common form of spinal fusion surgery, pedicle screws are installed in a series of consecutive spine segments. One or more rods are installed between the screws to secure the spinal segments with respect to one another. Once installed the consecutive spinal segments remain fixed with respect to one another, thereby allowing bone grafts to fuse to the spine, forming a solid bone.

In one example, spinal fusion surgery can be used to correct a spinal condition caused by spondylolisthesis in which broken bones or weakened joints allow a vertebra to slip forward and pinch a nerve root. In the context of this particular procedure, the lamina of the damaged vertebra and any remaining bone that may be pinching the nerve roots are removed. Bone grafts are then added to the sides of the spine joining the vertebrae above and below the damaged vertebra. Pedicle screws are installed in the vertebrae above and below the damaged vertebra. Rods are installed between the pedicle screws to prevent relative movement between the two spine segments, which allows the bone grafts to fuse to the spine, forming solid bone.

A typical pedicle screw includes an assembly with a rod retainer (or cup) pivotally mounted to the head of a screw. In conventional applications, the screw is installed in a spinal segment and the rod retainer remains exposed on the exterior of the spinal segment. The rod retainer includes structure that allows a rod to be fixedly secured to the pedicle screw assembly. For example, a conventional rod retainer may have a rod retainer slot and a set screw for securing the rod within the rod retainer slot. In use, a single rod may be secured between two or more pedicle screw assemblies to tie together the pedicle screw assemblies. The rod retainers are pivotally mounted to the heads of the screws to facilitate linking of the pedicle screw assemblies with a rod. More specifically, once the pedicle screws are installed in the spine, the rod retainers can be pivotally moved about the screw heads to bring the rod retainer slots into alignment to allow then to be joined by a single rod.

SUMMARY OF THE INVENTION

The present invention provides a pedicle screw assembly having an axial load element in the structure joining the screw to the rod retainer. In one embodiment, the pedicle screw assembly includes a screw that is pivotally joined to a rod retainer by a ball-and-socket joint. In this embodiment, the screw may include a ball and the rod retainer may include a socket configured to receive the ball. The assembly may include a saddle configured to mount within the rod retainer to secure the ball within the socket. The saddle may be configured to resiliently compress in the axial direction. For example, the saddle may define slots that create a spring within the body of the saddle to allow the saddle to resiliently compress in the axial direction. The slots may be formed in the saddle using a wire EDM process. Once installed, the saddle resiliently engages the ball with enough force to generally hold the rod retainer in place with respect to the screw, while still allowing manual movement of the rod retainer about the screw.

In one embodiment, the rod retainer is generally cup-shaped with a socket formed in the generally closed bottom of the cup. The rod retainer may define an opening through the bottom of the cup adjacent to the socket to allow the shaft of the screw to extend from the interior of the cup.

In one embodiment, the pedicle screw assembly includes a ball mounted to the head of the screw for pivotally seating the screw within the rod retainer. The ball may be an integral part of the head of the screw or it may be a split ball formed by two ball halves that are fitted over the head of the screw. The two ball halves may be configured to provide a generally spherical interface surface that is fitted closely within the socket.

In one embodiment, the saddle is generally tubular and includes a ball interface at one end and a rod interface at the other end. The saddle may include structure for securing the saddle within the interior of the rod retainer. The structure may include a pair of ears disposed near the rod interface end of the saddle. The interior surface of the rod retainer may include saddle attachment features capable of receiving the ears. For example, the saddle attachment features may include an annular ring for initial loading of the ears and a pair of scallops to seat the ears in a fully loaded position. The assembly may be configured to place sufficient load on the ball to hold the rod retainer in a given position on the ball, but not so much force that the rod retainer can not be manually pivoted about the ball, if desired.

In one embodiment, the saddle includes slots that render the saddle resilient in an axial direction. In one embodiment, the saddle includes a pair of slots extending partially across the saddle from opposite sides. The slots may be offset from one another in an axial direction to cooperatively provide a bridge section that joins the portions of the saddle on opposite sides of the slots. The characteristics of the slots may be selected to provide a bridge section that is resilient under the loads created by installing the saddle in the cup over the ball.

In one embodiment, the pedicle screw assembly includes a set screw for securing the rod in the rod retainer. The set screw may be threaded into the open end of the cup and may compress the rod against the rod interface in the end wall of the saddle. The set screw and rod retainer may have buttress threads to assist in bearing the high axial thrust created when the set screw is closed against the rod.

The present invention provides a simple and effective pedicle screw assembly that assists a surgeon by allowing the rod retainer to be manually adjusted about the head of the screw while helping to hold the rod retainer in a set position. In some embodiments, the axial load element is incorporated into the saddle element, thereby eliminating the need to manufacture and assemble additional parts. In some embodiments, the axial load element is formed by cutting slots in the body of the saddle. This is a simple, effective and reliable method for producing axial resiliency. In some embodiments, the saddle includes slots that are configured to provide rotational lockup between the upper and lower parts of the saddle. In some embodiments, the slots are configured to provide controlled axial compression of the saddle, thereby reducing the risk of the saddle binding within the rod retainer. In some embodiments, the saddle includes ears that facilitate installation of the saddle within the rod retainer under axial load. When combined with scallops (or similar structure) in the rod retainer, the ears allow the saddle to snap into place during assembly. In some embodiments, the annular ring and scallops further facilitate installation of the saddle within the rod retainer.

These and other features of the invention will be more fully understood and appreciated by reference to the description of the embodiments and the drawings.

BRIEF DESCRIPTION OF THE DRAWINGS

FIG. 4 is a perspective view of one half of a split ball.

FIG. 5 is a side view of one half of a split ball.

FIG. 6 is a sectional view of one half of a split ball.

FIG. 7 is a left side perspective view of a rod retainer.

FIG. 10 is a right side view of the rod retainer.

FIG. 11 is a top view of the rod retainer.

FIG. 15 is a front top perspective view of the saddle.

FIG. 16 is a front bottom perspective view of the saddle.

FIG. 17 is a front view of the saddle.

FIG. 18 is a left side view of the saddle.

FIG. 19 is a top view of the saddle.

FIG. 20 is a right side view of the saddle.

FIG. 21 is sectional view of the saddle taken along line 21-21 of FIG. 19.

FIG. 22 is a perspective view of the set screw.

FIG. 23 is a top view of the set screw.

FIG. 24 is a sectional view of the set screw taken along line 24-24 of FIG. 23.

FIG. 25 is a perspective view of an alternative pedicle screw assembly.

FIG. 26 is a perspective view of a second alternative pedicle screw assembly.

FIG. 27 is a side view of the second alternative pedicle screw assembly.

FIG. 28 is a sectional view of the second alternative pedicle screw assembly taken along line 28-28.

Figure 1:
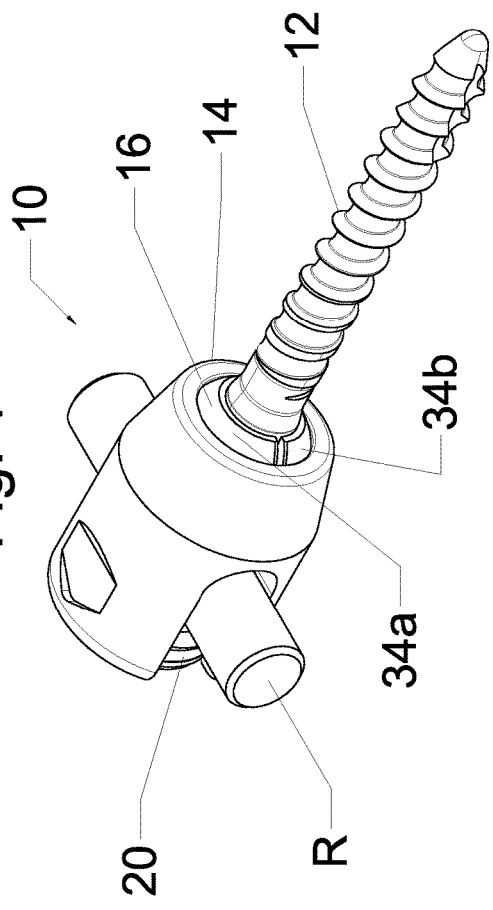
FIG. 1 is a perspective view of a pedicle screw assembly in accordance with an embodiment of the present invention.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations of those terms is meant to encompass the items listed thereafter and equivalents thereof as well as additional items and equivalents thereof.

DESCRIPTION OF CURRENT EMBODIMENTS

Figure 2:
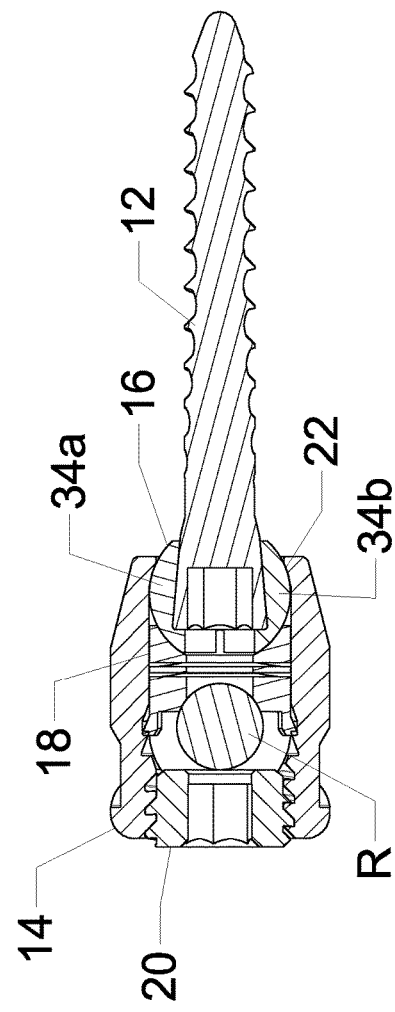
FIG. 2 is a sectional view of the pedicle screw assembly.

A pedicle screw assembly 10 according to an embodiment of the present invention is shown in FIGS. 1 and 2. The pedicle screw assembly 10 generally includes a screw 12, a rod retainer 14, a ball 16, a saddle 18 and a set screw 20. In this embodiment, the screw 12 is mounted to the rod retainer 14 via a ball-and-socket joint to allow the rod retainer 14 to be selectively movable with respect to the screw 12. In this embodiment, the ball 16 is disposed about the head of the screw 12 and pivotally received in a socket 22 in the rod retainer 14. Although the ball 16 of this embodiment is a split-ball, the present invention is also well suited for use with a screw having an integral ball (See FIGS. 26-28). The saddle 18 is fitted into the rod retainer 14 to secure the ball 16 in the socket 22. The saddle 18 is provided with resiliency in the axial direction to apply a bias to the ball-and-socket joint. The bias is small enough to allow the rod retainer 14 to be manually adjusted with respect to the screw 12, but great enough to hold the rod retainer 14 in a set position when not being adjusted.

Figure 3A:
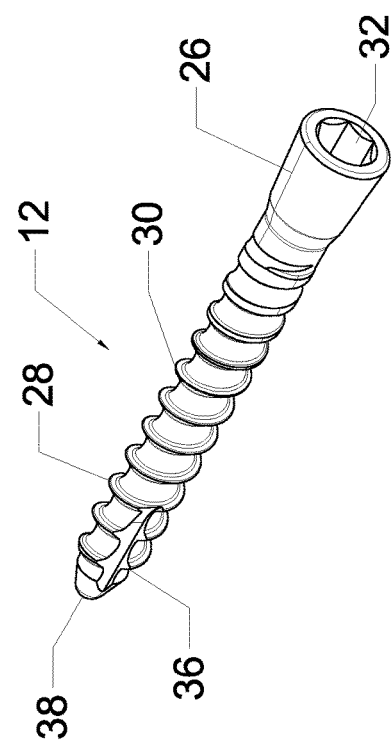
FIG. 3A is a perspective view of the screw.
Figure 3B:
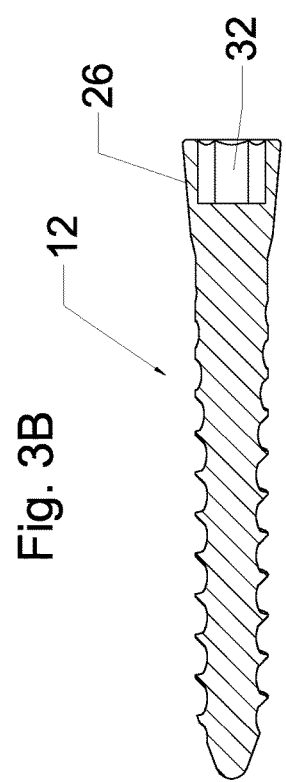
FIG. 3B is a sectional view of the head of the screw.
Figure 8:
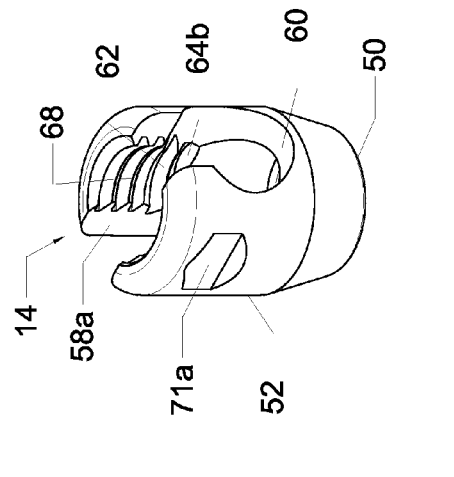
FIG. 8 is a right side perspective view of the rod retainer.
Figure 13:
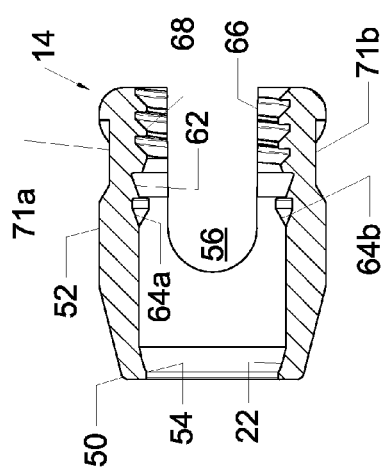
FIG. 13 is a sectional view of the rod retainer.
Figure 14:
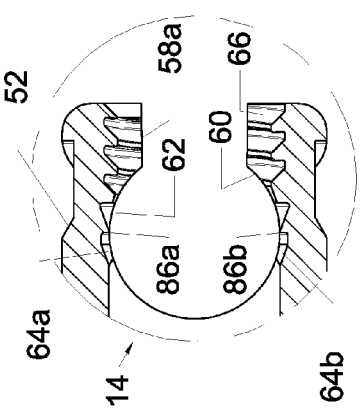
FIG. 14 is a sectional view of a portion of the rod retainer before the threads are cut.
Figure 9:
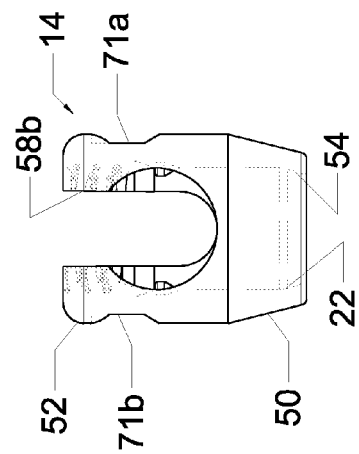
FIG. 9 is a front view of the rod retainer.
Figure 12:
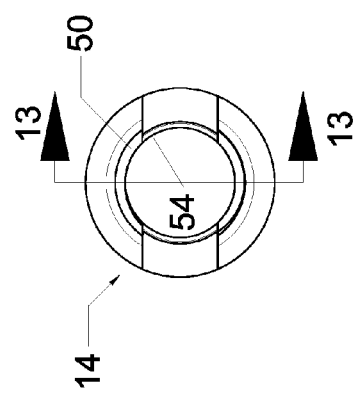
FIG. 12 is a bottom view of the rod retainer.

Referring now to FIGS. 3A and 3B, the screw 12 of the illustrated embodiment is generally conventional socket-head bone screw having a head 26, a shaft 28 and a helical thread 30. In this embodiment, the head 26 includes a tool interface that allows the screw 12 to be turned or driven. Although the tool interface may vary as desired, the tool interface in the illustrated embodiment is a hex socket 32. The hex socket 32 is configured to receive a conventional hex driver, such as a hex key or Allen key. In the illustrated embodiment, the ball 16 is formed from two split-ball halves 34a and 34b that are fitted over the head 26 of the screw 12. As a result, the exterior shape of the head 26 may be shaped to receive and interface with the two split-ball halves 34a and 34b, as described in more detail below. The shaft 28 may vary from application to application. However, in the illustrated embodiment, the shaft 28 extends from the head 26 and is tapered to a rounded tip 38. The details of the shaft 28 may vary from application to application. For example, the length, diameter, taper and tip of the shaft 28 may be selected based on the application. The thread 30 wraps helically around the shaft 28 from the tip 38 to a location near the head 26 of the screw 12. In the illustrated embodiment, the thread 30 is a generally conventional tapered, single-start course thread with a generally triangular cross-section. The thread 30 rises from the shaft 28 near the tip 38 and flattens back into the shaft 28 near head 26 (as shown in FIG. 3A). The form of the thread 30 may vary from application to application as desired. For example, the cross-sectional shape, angle, pitch, major diameter, minor diameter, pitch diameter, thread depth and taper may vary by application. In this embodiment, the screw 12 is a self-tapping screw having a self-tapping detail 36 disposed near the tip 38. As shown in FIG. 3A, the self-tapping detail 36 is defined by a gap in the continuity of the thread 30. The screw 12 need not be a self-tapping screw. The screw 12 may be manufactured from essentially any suitable material. For example, the screw 12 may be manufactured from titanium, stainless steel or other medically-suitable materials. As one example, FIG. 25 shows an alternative embodiment of the present invention in which the screw size is varied. The pedicle screw assembly 10' of FIG. 25 includes a screw 12', a rod retainer 14', a ball 16' and a set screw 20'. Although not shown in the FIG. 25, the assembly 10' also includes a saddle that is general identical to saddle 18. If desired, all of the components of the pedicle screw assembly 10' except for the screw 12' may be essentially identical to those of the pedicle screw assembly 10 shown in FIGS. 1-24. In applications with essentially identical components, the screw head of screw 12' may remain essentially the same as screw head 26 so that the screw 12' interfaces properly with the ball 16'.

As noted above, the rod retainer 14 is pivotally mounted to screw 12 to allow the rod retainer 14 to be adjusted for installation of the rod R. In the illustrated embodiment, the rod retainer 14 is coupled to the screw 12 by a ball-and-socket joint 24, where the ball 16 is disposed about the head 26 of the screw 12 and the socket 22 is defined in one end of the rod retainer 14. Referring now to FIGS. 1 and 2, the ball 16 of this embodiment is defined by a pair of split-ball halves 34a and 34b. In this embodiment, the two split ball halves 34a and 34b are generally identical and are configured to close on and entrap the head 26 of the screw 12 (See FIGS. 4-6). Each split ball 34a-b has generally semi-spherical outer surface 40a-b, an internal screw-head void 42a-b and socket-head opening 44a-b. When the two split ball halves 34a-34b are brought together over the screw head 26, they cooperatively define a generally spherical ball configured to interface with the socket 22 in the rod retainer 14. The screw-head void 42a-b of this embodiment is shaped to receive approximately one-half of the screw head 26. The size, shape and configuration of the screw-head void 42a-b may vary from application to application to operate with different screw heads. The socket-head opening 44a-b is shaped to provide the assembled ball 16 with a passage for accessing the tool interface in the head 26 of the screw 12. This allows the screw 12 to be installed even when the ball 16 is assembled over the screw head 26. In this embodiment, the socket-head opening 44a-b is a generally semi-circular opening sized and shaped to allow a hex drive to be fitted into the screw head 26. The size, shape and configuration of the socket-head opening 44a-b may vary from application to application. Although the illustrated embodiment includes a split-ball, the present invention is well-suited for use with applications that do not include a split-ball. For example, the present invention may be incorporated into a screw assembly in which the ball is formed directly into the screw head or the ball is formed from a single piece mounted to the screw head. In some embodiments, it may be possible to drive the screw by directly engaging the ball with a drive tool.

In the illustrated embodiment, the rod retainer 14 is pivotally mounted to the screw head 26 and includes a structure for connecting to a rod R. Referring now to FIG. 7, the rod retainer 14 of this embodiment is generally cup-shaped having a bottom 50 and a circumferential wall 52. The interior surface of the bottom 50 defines the socket 22 to receive the ball 16. The bottom 50 also defines through-hole 54 of sufficient diameter for the screw 12 to extend from the rod retainer 14. In the illustrated embodiment, the internal diameter of the through-hole 54 is substantially greater than the external diameter of the shaft 28 to allow the rod retainer 14 to pivot about the screw head 26. The circumferential wall 52 is generally tubular and cooperates with the bottom 50 to define an internal void 56 configured to receive the ball 16, the saddle 18, the rod R and the set screw 20. The circumferential wall 52 defines a pair of assembly slots 58a-b. The assembly slots 58a-b are of sufficient size to allow the rod R to be fitted into the rod retainer 14 in engagement with the saddle 18, as described in more detail below. In the illustrated embodiment, one of the assembly slots 58a defines an enlarged central opening 60 for fitting the split ball halves 34a-b into the interior of the rod retainer 14. As shown, the rod retainer 14 of FIGS. 7-14 includes an enlarged circular central opening 60 of sufficient size to allow the split ball halves 34a-b to be separately fitted into the internal void 56 and fitted onto the head 26 of the screw 12 (See FIG. 10). The circumferential wall 52 may include structure for securing the saddle 18 in the rod retainer 14. Although the structure may vary, in the illustrated embodiment, the circumferential wall 52 defines an annular groove 62 and a pair of scallops 64a-b used to install the saddle 18. The annular groove 62 opens into the assembly slots 58a-b, and the scallops are axially offset from the annular groove 62 toward bottom 50. As described in more detail below, the ears 72a-b of the saddle 18 may be initially loaded into the annular groove 62 and then pressed from the annular groove 62 down into the scallops 64a-b. The upper walls 86a-b of the scallops 64a-b may extend substantially perpendicularly to the axis of the rod retainer 14 (86a-b) to provide a surface suitable for retaining the ears 72a-b of the axially loaded saddle 18. The size, shape and configuration of the scallops 64a-b may vary from application to application depending on the specifics of the saddle 18 and desired axial load. As perhaps best shown in FIGS. 1, 2 and 7, the upper end of the circumferential wall 52 may define a mouth 66 configured to receive the rod R and the set screw 20. The internal surface of the circumferential wall 52 may include a thread 68 beginning at the mouth 66 to provide a mechanism for installing the set screw 20 in the rod retainer 14. To withstand high axial loads, the internal thread 68 may be a buttress thread. The exterior of the rod retainer 14 may be shaped to provide a pair of opposed parallel surfaces 71a-b. The parallel surfaces 71a-b may provide a place to engage the rod retainer 14 with a tool for holding and/or aligning the rod retainer 14.

As noted above, the pedicle screw assembly 10 of the present invention includes a saddle 18 that is fitted into the rod retainer 14 to entrap the ball 16. The saddle 18 is generally tubular and includes a circumferential body 72 with a pair of ears 74a-b for installing the saddle 18 within the rod retainer 14 (See FIG. 15-21). The body 72 of the illustrated embodiment has an outer diameter that closely corresponds with the inner diameter of the circumferential wall 52 of the rod retainer 14. The upper end of the body 72 includes a rod seat 76 shaped to receive the rod R (See FIG. 2). For example, as shown in FIG. 15, the rod seat 76 may be a centrally-located cylindrical depression having a radius slightly larger than that of the rod R. The size, shape and figuration of the rod seat 76 may vary from application to application. For example, the shape of the rod seat 76 may vary to correspond with different rods. In this embodiment, the lower end of the body 72 includes a ball seat 78. The ball seat 78 of the illustrated embodiment is a generally spherical depression that corresponds with the spherical outer surface of the ball 16. For example, the ball seat 78 may be a partial sphere having a radius that is slightly larger than the radius of the ball 16. The size, shape and configuration of the ball seat 78 may vary from application to application. The saddle 18 defines an internal through-hole 80 providing access to the head 26 of the screw 12. The through-hole 80 of this embodiment is generally cylindrical and extends coaxially through the body 72 with a diameter sufficient to allow a drive tool to be inserted into the screw head 26 through the saddle 18. The ears 72a-b extend from the upper end of the body 72 and are angled outwardly to engage the annular groove 62 and the scallops 646a-b. The ears 72a-b are configured to be sufficiently elastic and resilient to bend inwardly under force to allow them to be snapped fitted into the scallops 64*a-b*. The leading surface 82*a-b* of each ear 72*a-b* is inclined with respect to the axis of the saddle 18 to facilitate inward flexing of the ears 72*a-b* during installation. The trailing end 84*a-b* of each ear 72*a-b* is generally perpendicular to the axis of the saddle 18. In use, the perpendicular surfaces 84*a-b* of the ears 72*a-b* engage the corresponding perpendicular upper wall 86*a-b* in the scallops 64*a-b* to resist removal of the ears 72*a-b* from the scallops 64*a-b*.

As noted above, the pedicle screw assembly 10 is provided with a load element that provides elastic resiliency in the axial direction. The axial load element allows the ball 16 to be resiliently engaged within the socket 22. The axial load may vary from application to application, but is typically selected to provide enough force to generally hold the rod retainer 14 is a fixed position with respect to the screw head 26, while still allowing the rod retainer 14 to be manually moved as desired. In use, the axial load facilitates installation and use of the pedicle screw assembly 12 because it holds the rod retainer 14 in a desired position in the absence of external forces. In the illustrated embodiment, the saddle 18 is configured to function as the load element providing elastic resiliency in the axial direction. As shown, the saddle 18 of this embodiment includes a pair of slots 90*a-b* that extend partially across the saddle 18 from opposite sides to create an interconnecting bridge section 92 (or spring) that is resilient under the loads expected when the saddle 18 have been loaded into the rod retainer 14. In use, the bridge section 92 functions as an integrated spring that allows the saddle 18 to resiliently compress in the axial direction. In this embodiment, the slots 90*a-b* extend into the body 72 from opposite sides in a direction that is generally perpendicular to the axis of the saddle 18 (See FIGS. 17 and 21). The slots 90*a-b* are axially offset from one another by a distance selected to provide a bridge section 92 of the desired strength and resiliency. Although generally perpendicular to the longitudinal axis of the saddle 18, the slots 90*a-b* of the illustrated embodiment are curved at opposite ends to provide the bridge section 92 with curved portions 94*a-b*. The curved portions 94*a-b* are optional, but when used can help to provide a variety of benefits. For example, the curved portions may provide a rotational lockup when the saddle 18 is compressed, thereby resisting rotational movement between the top and bottom parts of the saddle 18 (i.e. the parts above and below the slots 90*a-b*). As another example, the curved portions can help to balance the amount of material above and below the slots 90*a-b*. Further, the shape of the slots 90*a-b* can be selected to control and maximize the bearing surface as the saddle 18 is compressed. In use, the thin sections that join the bridge section 92 to the remainder of the body of the saddle 18 function as initial fulcrums for the saddle 18. Under sufficient axial load, the surfaces above and below the slots come into initial contact, thereby creating new fulcrum points opposite the initial fulcrums. Under further compression, the new fulcrums overcome the initial fulcrums. The thin sections begin to crush, compact and/or deform. At full compression, the thin sections may be almost completely crushed, compacted and/or deformed and the slots 90*a-b* may be almost completely closed on both ends. In this embodiment, the slots 90*a-b* provide elastic resiliency under loads expected in the assembled screw assembly 10. However, it is not necessary for the bridge section 92 to remain resilient after installing a rod R in the rod retainer 14. Instead, the bridge section 92 may, as described above, permanently deform under the greater loads encountered when the set screw 20 is tightened to lock rod R in place in the rod retainer 14. As such, it should be recognized that a saddle 18 or other axial load member that loses some or all of its axial resiliency when placed under compression is within the scope of the present invention. The size, shape and configuration of the slots may vary from application to application. For example, the width of the slots, the number of slots, the shape of the slots, the axial spacing between the slots and the dimensions of the thin sections (or lands) joining the bridge section 92 to the remainder of the saddle 18 may vary as desired to tune the saddle 18 for a specific application. To illustrate this point, the configuration of the slots may vary to control the axial resiliency of the saddle 18 and/or to control the rotational interlock between the upper and lower portions of the saddle 18. In the illustrated embodiment, the slots 90*a-b* may be formed using an electric discharge machine ("EDM"), such as a wire EDM machine. For example, the slots 90*a-b* may be cut into the saddle 18 in separate passes of the wire EDM machine. Alternatively, the slots may, depending on their configuration, be formed using other techniques and apparatus, including without limitation various conventional and non-conventional machining technologies, such as turning, milling, grinding, drilling, sinker EDM, electrochemical machining ("ECM"), water jet cutting and laser cutting.

Referring now to FIG. 2, the specifications of the various components are selected so that the saddle 18 is placed under an axial load when installed in the rod retainer 14. For example, the various components may be configured so that the distance between the scallops and the ball 16 is slightly smaller than the distance from the ears to the ball seat 78. As a result, the saddle 18 is compressed slightly in an axial direction when it is installed in the rod retainer 14 over the ball 16. The axial load on the joint between the rod retainer 14 and the screw 12 is selected, in the illustrated embodiment, to create sufficient friction in the system to hold the rod retainer 14 in a set position with respect to the screw 12 in the absence of any external force, while still allowing the rod retainer 14 to be manually pivoted and/or rotated as desired to align the rod retainer with the rod retainer of one or more other pedicle screw assemblies. As noted above, the amount of axial load provided by the saddle can be adjusted by varying one or more of a variety of details, such as the position of the scallops, the position of the socket, the length of the ears, the characteristics of the bridge section and the length of the saddle. As shown in FIG. 2, the split ball halves engage one another along a plane that extends along the axis of the screw. In the assembled pedicle screw assembly 10, the ball seat 78 engages both of the split ball halves in such a way that the axial load in the saddle 18 urges together the split ball halves.

In the illustrated embodiment, the saddle 18 is configured to function as the axial load element. In the illustrated embodiment, the axial resiliency is provided by slots that form a "spring" integrated directly into the saddle 18. Axial resiliency may be integrated into the saddle in other ways, such as by incorporating one or more slots in other locations in the body 72 and/or by providing axial resiliency to the ears 74*a-b*. The axial load element may be separate from the saddle 18, if desired. For example, a separate axial load element may be disposed between the saddle 18 and the ball 16 and/or between the saddle 18 and the rod retainer 14. The axial resiliency may be provided by a spring or other resilient structure incorporated into the pedicle screw assembly. For example, axial resiliency may be provided by a disc spring, a conical spring washer, a wave spring washer, a coil spring or a mass of resilient material.

As described above, the rod R may be fixed to the rod retainer 14 by a rod locking structure. In this embodiment, the rod locking structure is a set screw 20 configured to be installed in the mouth 66 of the rod retainer 14. Referring now to FIGS. 22-24, the set screw 20 may be generally disc-shaped and have an external thread 96 configured to threadedly interface with the thread on the inside of the circumferential wall of the rod retainer 14. As with the rod retainer 14, the set screw 20 may utilize a buttress thread that is configured to withstand the large axial forces generated by tightening the set screw 20 against the rod R. The set screw 20 also includes a tool interface configured to receive a mounting tool for driving the set screw 20. For example, the set screw 20 may include a hex socket 98 configured to receive a hex drive. In the illustrated embodiment, the set screw 20 also defines a through-hole 99 of sufficient diameter to allow a tool to pass through the set screw 20 into the screw head 26. In this embodiment, the hex socket 98 of the set screw 20 is substantially larger than the hex socket 32 of the screw 12 so that the tool for securing the screw 12 can be fitted through and rotated freely within the hex socket 98 and through-hole 99. Although the illustrated embodiment includes a set screw 20 that intersecures the rod R and the rod retainer 14, the set screw 20 may be replaced by essentially any structure capable of intersecuring the rod R and the rod retainer 14.

Assembly of the pedicle screw assembly of the illustrated embodiment will now be described. To begin assembly, the rod retainer 14 is fitted over the head 26 of the screw 12. For example, if the through-hole 54 in the rod retainer 14 is larger than the screw head 26, the rod retainer 14 can be fitted over the screw head 26. The two split ball halves 34*a-b* are fitted into the rod retainer 14 through the central opening 60 and are closed together over the screw head 26. The assembled split ball halves 34*a-b* and screw head 26 are fitted into the socket 22 in the interior of the rod retainer 14. The saddle 18 is fitted into the rod retainer 14 by aligning ears 72*a-b* with the assembly slots 58*a-b* and moving the saddle 18 down axially into the rod retainer 14 until the ears 72*a-b* are axially aligned with annular groove 62. The saddle 18 is then initially loaded into the rod retainer 14 by rotating the saddle 18 approximately 90 degrees with respect to the rod retainer 14 to move the ears 72*a-b* into the annular groove 62 in alignment with the scallops 64*a-b*. The saddle 18 is then fully loaded by moving the rod retainer 14 further down axially into the rod retainer 14 until the ears 72*a-b* engage the scallops 64*a-b*. During this final loading stage, the ears 72*a-b* flex inwardly to allow the ears 72*a-b* to pass from the annular groove 62 and then spring back outwardly to interlock with the scallops 64*a-b*. This also causes the ball seat 78 to come into engagement with the ball 16. As noted above, the pedicle screw assembly 10 components are configured so that the fully loaded saddle 18 is contained in the rod retainer 14 under an axial load. More specifically, the distance from the ears 72*a-b* to the base of the ball seat 78 is slightly larger than the distance from the scallops 64*a-b* to the ball 16. As a result, the saddle 18 is forced to resiliently compress in the axial direction as it is moved from the initial loading position in the annular groove 62 into fully loaded position in the scallops 64*a-b*. The resiliency of the saddle 18 and the amount of axial load provided by the saddle 18 may be varied by adjusting one or more of a variety of characteristics of the pedicle screw assembly 10, such as the relative position between the scallops 64*a-b* and the socket 22, the characteristics of the ball 16, the axial length of the saddle 18 and/or the characteristics of the ears 72*a-b*, as well as the size, shape, arrangement and configuration of the slots 90*a-b*. In the illustrated embodiment, the saddle 18 is configured to apply enough load to the ball-and-socket joint to create sufficient friction within the assembly to generally hold the rod retainer 14 in place on the screw 12. The load is, however, selected to be small enough to allow the rod retainer 14 to be swiveled or otherwise moved about on the ball 16 manually without the use of any tools. This allows a surgeon to move the rod retainer 14 into the desired position where it will generally stay unless acted on by an outside force. In typical applications, at least two pedicle screw assemblies will be connected by a rod R. The rod retainers 14 of the two pedicle screw assemblies 10 are oriented in sufficient alignment to allow a single rod R to be fitted through both. The rod R is fitted into the two rod retainers 14 through the assembly slots 58*a-b* and positioned in the rod seat 76 in the saddle 18. The rod R is secured to both pedicle screw assemblies 10 by installing set screws 20. The set screws 20 are fitted into the mouth 66 (if not already present) and tightened with sufficient force to drive the rod R down into the saddle 18, the saddle 18 into the ball 16 and the ball 16 into the socket 22. Typically, the force applied by the set screws 20 is sufficient to fully compress the saddle 18 in the axial direction and effectively render the ball-and-socket joint immobile, thereby securing the rod retainer 14 against further movement with respect to the screw head 26.

FIGS. 26-28 show another embodiment in which the pedicle screw assembly is "top loaded." Except as otherwise described, the pedicle screw assembly 10" of this embodiment is essentially identical to pedicle screw assembly 10 described above. The assembly 10" generally includes a screw 12", a rod retainer 14", a saddle 18" and a set screw (not shown). The screw 12" includes an integral ball 16" disposed at or about the head 26". A tool interface 32 is formed in the head 26". As with pedicle screw assembly 10, the ball 16" of this assembly 10" is fitted into a socket 22" in the rod retainer 14" to form a ball-and-socket joint. As perhaps best shown in FIG. 28, the saddle 18" of this embodiment is essentially identical to saddle 18, including a circumferential body 72" with a pair of ears 74*a-b"* for installing the saddle 18" within the rod retainer 14", as well as a pair of slots 90*a-b"* that provide the saddle 18" with axial resiliency. The rod retainer 14" includes an annular groove 62" and a pair of scallops 62*a-b"* for installing the saddle 18" as described above in connection with pedicle screw assembly 10. The The pedicle screw assembly 10" is assembled by fitting the screw 12" shaft-first through the rod retainer 14" until the ball 16" is seated in socket 22". The saddle 18" may then be installed in the rod retainer 14" as described above in connection with pedicle screw assembly 10. Suffice it to say that the saddle 18" is oriented so that the ears 74*a-b"* are aligned with slots 58*a-b"* and then the saddle 18" is fitted down into the rod retainer 14". The saddle 18" is inserted in the rod retainer 14" until the ears 74*a-b"* are aligned with the annular groove 62", and then it is rotated 90 degrees so that the ears 74*a-b"* pass into the annular groove 62". The saddle 18" is then further inserted into the rod retainer 14" until the ears 74*a-b"* snap into place in the scallops 62*a-b"*. The characteristics of the ball 16", rod retainer 14" and saddle 18" are selected so that, once installed, the saddle 18" applies sufficient axial load to the ball-and-socket joint to create sufficient friction to generally hold the rod retainer 14" in place on the screw 12". The load is, however, selected to be small enough to allow the rod retainer 14" to be swiveled or otherwise moved about on the ball 16" manually without the use of any tools. During use, a rod (not shown)

may be installed in the rod retainer 14″ using a set screw (not shown) as described above in connection with pedicle screw assembly 10.

The above description is that of current embodiments of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular. This disclosure is presented for illustrative purposes and should not be interpreted as an exhaustive description of all embodiments of the invention or to limit the scope of the invention to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits.

The embodiments of the invention in which an exclusive property or privilege is claimed are defined as follows:

1. A pedicle screw assembly comprising:
   a screw;
   a rod retainer configured to selectively receive a rod, said rod retainer pivotally joined to said screw at a joint;
   a saddle disposed within said rod retainer, said saddle including at least one slot formed into said saddle and extending in a generally transverse direction to provide said saddle with resiliency in an axial direction and said saddle applying a resilient bias to said joint in an axial direction, said bias tending to hold said rod retainer in place with respect to said screw at said joint, wherein said saddle includes at least two ears for interlocking said saddle within said rod retainer; and
   a rod locking structure configured to secure a rod to said rod retainer,
   wherein said rod retainer defines an annular groove configured to receive said ears, said saddle being rotatable within said rod retainer when said ears are disposed within said annular groove, and
   wherein said rod retainer defines at least two recesses configured to receive said at least two ears, said recesses axially offset from said annular groove, whereby said saddle may be moved axially within said rod retainer to move said ears from said annular groove into said recesses.

2. The assembly of claim 1 wherein said joint is a ball-and-socket joint.

3. The assembly of claim 2 wherein said ball-and-socket includes a ball disposed about a head of said screw and a socket defined within said rod retainer.

4. The assembly of claim 3 wherein said ball includes two split ball halves closed about said screw head, said saddle configured to engage and assist in retaining together said split ball halves.

5. The assembly of claim 3 wherein said saddle is fitted within and secured to said rod retainer to hold said ball within said socket.

6. The assembly of claim 1 wherein said saddle includes a pair of axially offset slots formed into said saddle and extending in a generally transverse direction, said slots cooperatively defining a resilient bridge section to provide said saddle with resiliency in said axial direction.

7. The assembly of claim 6 wherein said slots are defined in said saddle from opposite directions.

8. The assembly of claim 7 wherein said saddle includes a ball seat at one end and a rod seat at an opposite end.

9. A pedicle screw assembly comprising:
   a screw with a shaft and a head, said screw having a ball at said head;
   a rod retainer mounted to said screw, said rod retainer defining a socket receiving said ball, said rod retainer being pivotally movable about said ball; and
   a saddle installed within said rod retainer to secure said ball in said socket, said saddle includes first and second slots formed into the saddle and extending generally transversely into said saddle from opposite sides, said first and second slots being axially offset from one another to define a bridge section that provides said saddle with resiliency in an axial direction and being installed under an axial load, whereby said saddle provides a bias compressing said ball within said socket in an axial direction to hold said rod retainer in a fixed position relative to said screw in an absence of an external force, wherein said saddle includes at least two ears for interlocking said saddle within said rod retainer; and
   wherein said rod retainer defines an annular groove configured to receive said ears, said saddle being rotatable within said rod retainer when said ears are disposed within said annular groove, and
   wherein said rod retainer defines at least two recesses configured to receive said at least two ears, said recesses axially offset from said annular groove, whereby said saddle may be moved axially within said rod retainer to move said ears from said annular groove into said recesses.

10. The assembly of claim 9 wherein said saddle includes a first end defining a rod seat and a second end defining a ball seat, said rod seat configured to seat a rod for connecting the pedicle screw to a rod, said ball seat configured to pivotally engage said ball.

* * * * *